United States Patent
Suda et al.

(10) Patent No.: US 12,111,311 B2
(45) Date of Patent: Oct. 8, 2024

(54) PARTICLE, PARTICLE FOR AGGLUTINATION METHOD, AND REAGENT, KIT AND DETECTION METHOD CONTAINING THE SAME

(71) Applicants: CANON KABUSHIKI KAISHA, Tokyo (JP); CANON MEDICAL SYSTEMS CORPORATION, Tochigi (JP)

(72) Inventors: Sakae Suda, Yokohama (JP); Masao Suzuki, Kawasaki (JP); Kazumichi Nakahama, Tokyo (JP); Keiichiro Tsubaki, Tokyo (JP); Kengo Kanazaki, Yokohama (JP); Ryo Natori, Tokyo (JP); Fumio Yamauchi, Yokohama (JP)

(73) Assignees: CANON KABUSHIKI KAISHA, Tokyo (JP); CANON MEDICAL SYSTEMS CORPORATION, Tochigi (JP)

( * ) Notice: Subject to any disclaimer, the term of this patent is extended or adjusted under 35 U.S.C. 154(b) by 921 days.

(21) Appl. No.: 16/986,662

(22) Filed: Aug. 6, 2020

(65) Prior Publication Data
US 2021/0055292 A1 Feb. 25, 2021

(30) Foreign Application Priority Data
Aug. 23, 2019 (JP) .................. 2019-153203

(51) Int. Cl.
*G01N 33/543* (2006.01)
*C08F 20/26* (2006.01)
*C08F 212/08* (2006.01)
*C08F 220/32* (2006.01)
*C08F 220/34* (2006.01)
*C08F 220/38* (2006.01)
*C08L 33/06* (2006.01)
*G01N 33/547* (2006.01)

(52) U.S. Cl.
CPC ..... *G01N 33/54353* (2013.01); *C08F 212/08* (2013.01); *C08F 220/346* (2020.02); *C08F 220/382* (2020.02); *G01N 33/54313* (2013.01); *G01N 33/547* (2013.01); *C08F 20/26* (2013.01); *C08F 220/325* (2020.02); *C08L 33/068* (2013.01)

(58) Field of Classification Search
CPC ............ G01N 33/54353; C08F 212/08; C08F 220/325; C08L 33/068
See application file for complete search history.

(56) References Cited

U.S. PATENT DOCUMENTS 5,986,072 A 11/1999 Handa et al.
6,545,132 B1 4/2003 Handa et al.
6,703,207 B2 3/2004 Handa et al.
7,632,688 B2 12/2009 Oka et al.
10,139,401 B2 11/2018 Kai et al.
2002/0160472 A1 10/2002 Handa et al.
2010/0034748 A1* 2/2010 Li ................... A61K 49/0032
  424/9.4
2016/0069871 A1* 3/2016 Ueya ................... C08F 292/00
  435/6.1
2021/0055286 A1 2/2021 Suzuki et al.

FOREIGN PATENT DOCUMENTS

| JP | 2000-351814 A | | 12/2000 |
|----|---|---|---|
| JP | 2004-331953 A | | 11/2004 |
| JP | 2005-232237 A | | 9/2005 |
| JP | 2009-031130 A | | 2/2009 |
| JP | 2016125948 A | * | 7/2016 |
| WO | 2015/119288 A1 | | 8/2015 |
| WO | 2021/039982 A1 | | 3/2021 |

OTHER PUBLICATIONS

Machine translation of JP-2016125948-A as obtained by Patentscope. (Year: 2016).*
Xu, M. et al. "Polar Polymeric Stationary Phases for Normal-Phase HPLC Based on Monodisperse Macroporous Poly(2,3-dihydroxypropyl methacrylate-co-ethylene dimethacrylate) Beads". Anal. Chem. 2003, 75, 4, 1011-1021. (Year: 2003).*
J. Koubkova, "Magnetic poly(glycidyl methacrylate) microspheres for protein capture", New Biotechnology, 31, 5, 482-491. (Year: 2014).*
Suzuki et al., U.S. Appl. No. 16/986,649, filed Aug. 6, 2020.
Natori et al., U.S. Appl. No. 17/667,823, filed Feb. 9, 2022.
Non-final Office Action in U.S. Appl. No. 16/986,649 (Aug. 2023).
Taro Akazawa et al., "Application of Hydrogel Microspheres to Latex Diagnosis," 50(5) Jpn. J. Polym. Sci. Technol. (Kobunshi Ronbunshu) 431-435 (May 1993).

(Continued)

*Primary Examiner* — Kregg T Brooks
*Assistant Examiner* — David R. Foss
(74) *Attorney, Agent, or Firm* — Venable LLP

(57) ABSTRACT

The present disclosure provides a particle showing a small non-specific adsorption, having a reactive functional group for chemically bonding a ligand thereto, and being suitable for an agglutination method; a particle for the agglutination method having a ligand chemically bonded to the particle; a reagent, a kit and a method for detecting a target substance, each for in vitro diagnosis, each of which contains the particle. The particle includes a polymer having a unit having a linker A in a side chain, wherein when both terminals of the linker A are represented by X1 and X2, the linker A has a reactive functional group for chemically bonding a ligand thereto in one of X1 and X2; one of X1 and X2 includes an ester structure; and a sum of bonds between atoms linearly connecting X1 and X2 is 18 to 24 and the X1 and X2 contain $CH_2$ or CH.

16 Claims, No Drawings

(56) References Cited

OTHER PUBLICATIONS

Notice of Reasons for Refusal in Japanese Application No. 2019-153203 (Sep. 2023).
Final Office Action in U.S. Appl. No. 16/986,649 (Mar. 2024).

* cited by examiner

PARTICLE, PARTICLE FOR AGGLUTINATION METHOD, AND REAGENT, KIT AND DETECTION METHOD CONTAINING THE SAME

BACKGROUND OF THE DISCLOSURE

Field of the Disclosure

The present disclosure relates to: a particle; an affinity particle for an agglutination method having a ligand for a target substance bonded thereto; and a reagent, a kit and a method for detecting a target substance, each for in vitro diagnosis, each of which contains the particle.

Description of the Related Art

As a simple and rapid immunoassay method, agglutination methods, inter alia, a latex agglutination method, can be mentioned. In this method, a dispersion liquid of particles for the latex agglutination method, which are each chemically bonded to a ligand having affinity for a target substance, is mixed with a specimen that possibly contains the target substance. On this occasion, if the target substance is contained in the specimen, the particles for the latex agglutination method cause an agglutination reaction, and accordingly, the presence or absence of a disease can be identified, by optically detecting the agglutination reaction as amounts of changes in an intensity of scattered light, an intensity of transmitted light, an absorbance and the like. In general, an antibody and an antigen, or an antigen and an antibody are used for a combination of a ligand and a target substance. It is desired for a particle constituting the particles for the latex agglutination method that a characteristic of adsorbing a substance other than the target substance is small, which is so-called non-specific adsorption, for the purpose of not causing a non-specific agglutination reaction that does not originate from the target substance.

As a procedure for reducing the non-specific adsorption of the particle, there is a method of coating a surface of the particle with a biologically-derived substance such as albumin, casein and gelatin. However, there is the case where the physical properties of these biologically-derived substances are different depending on each production lot, and in addition, opinions are also heard that there are concerns about future biological contamination due to the use thereof in large quantities.

A procedure of coating the surface of the particle with an amphiphilic polymer compound is also effective as a method for reducing the non-specific adsorption, but the adsorption of the polymer compound to the particle originates in physical adsorption, and accordingly, there is a possibility that the particle may be liberated due to dilution; and sometimes the non-specific adsorption cannot be suppressed sufficiently.

In Bioseparation using affinity latex (1995) p11 to p30, a particle is disclosed which has polyglycidyl methacrylate arranged on the surface. It is known that the polyglycidyl methacrylate arranged on the surface of the particle shows a glycol by a part of the glycidyl group being opened, and thereby suppresses the non-specific adsorption.

In addition, in Japanese Patent Application Laid-Open No. 2000-351814 and Japanese Patent Application Laid-Open No. 2005-232237, a particle is disclosed in which a reactive functional group or a ligand is chemically bonded to a particle on the surface of which polyglycidyl methacrylate is arranged, via a linker.

SUMMARY OF THE DISCLOSURE

When the present inventors chemically bonded a ligand to the particle of the Bioseparation using affinity latex (1995) p11 to p30, sufficient dispersion stability could not be guaranteed in many general aqueous buffer solutions, and it was difficult to use the particle as the particles for the agglutination method. On the other hand, when the present inventors attempted to chemically bond a ligand to a particle which was synthesized according to Japanese Patent Application Laid-Open No. 2000-351814 and to use the particle as the particle for the agglutination method, the non-specific adsorption was surprisingly suppressed, but the dispersion stability was excessively excellent, and accordingly sufficient aggregation reaction could not be observed in some cases. The reason why the particle described in Japanese Patent Application Laid-Open No. 2000-351814 is superior in dispersion stability to the particle described in Bioseparation using affinity latex (1995) p11 to p30 is considered to be caused by an exclusion volume effect between the particles, which originates in a linker.

The present disclosure has been made in view of these background arts and problems. An object of the present disclosure is to provide a particle that shows a small non-specific adsorption, has a reactive functional group for chemically bonding a ligand thereto, and is suitable for an agglutination method; and a reagent, a kit and a detection method, which contain the particle.

Specifically, a first aspect of the present disclosure relates to a particle including a polymer having a unit having a linker A in a side chain, wherein when both terminals of the linker A are represented by X1 and X2, the linker A has a reactive functional group for chemically bonding a ligand thereto in one of X1 and X2; one of X1 and X2 of the linker A includes an ester structure; and a sum of bonds between atoms, which linearly connect X1 and X2 of the linker A, is in a range of 18 or more and 24 or less, wherein the X1 and X2 contain $CH_2$ or CH.

A second aspect of the present disclosure relates to a particle for an agglutination method having a ligand chemically bonded to the particle via the linker A.

A third aspect of the present disclosure relates to a reagent for use in detecting a target substance in a specimen by in vitro diagnosis, including the particle for the agglutination method; a kit for use in detecting the target substance in the specimen by in vitro diagnosis, including at least the reagent; and a detection method, including mixing the particles for the agglutination method with the specimen that possibly contains the target substance.

Further features of the present disclosure will become apparent from the following description of exemplary embodiments.

DESCRIPTION OF THE EMBODIMENTS

Preferred embodiments of the present disclosure will now be described in detail.

Embodiments of the present disclosure will be described below in detail, but the technical scope of the present disclosure is not limited to these embodiments.

The present disclosure is a particle including a polymer having a unit having a linker A in a side chain, wherein both terminals of the linker A are denoted by X1 and X2, the linker A has a reactive functional group for chemically bonding a ligand thereto in one of X1 and X2; one of X1 and X2 of the linker A includes an ester structure (COO); and a sum of bonds between atoms, which linearly connect X1 and X2 of the linker A, is in a range of 18 or more and 24 or less, wherein the X1 and X2 contain $CH_2$ or CH. Here, the "unit" means a unit structure which corresponds to one monomer.

The reactive functional group exists on a surface of the particle and functions for chemically bonding to the ligand, and is not particularly limited in a range in which the object of the present disclosure can be achieved. Examples of the reactive functional groups include a carboxyl group, an amino group, a thiol group and an active ester group, but the present disclosure is not limited to the groups. However, in consideration of versatility and chemical stability, it is preferable for the reactive functional group to be a carboxyl group or a salt of a carboxyl group, and when the particles of the present disclosure are stored as an aqueous dispersion liquid while the dispersion stability is kept, is more preferable to be a salt of the carboxyl group. Examples of the salt include a metal salt such as a sodium salt or a potassium salt, and an organic salt such as an ammonium salt, but in consideration of reactivity at the time when the reactive functional group and the ligand are chemically bonded, it is more preferable that the salt is a salt neutralized by an organic salt. Examples of the chemical compound which forms the organic salt of the carboxyl group include ammonia, diethylamine, triethylamine, ethanolamine and diethylamino ethanol, but the present disclosure is not limited to the examples. Considering experimental operability such as a boiling point and solubility in various solvents, triethylamine is easy to use. Chemical compounds that form an organic salt of the carboxyl group may be used alone or in combination of two or more types, in a range in which the object of the present disclosure can be achieved. Similarly, a chemical compound that forms a metal salt may be used in combination with a chemical compound that forms an organic salt.

The greatest feature of the present disclosure is the length of a chain of the linker A. Specifically, the present disclosure is characterized in that, when both terminals of the linker A are represented by X1 and X2, the sum of bonds between atoms, which linearly connect X1 and X2, is in a range of 18 or more and 24 or less. Here, the bond means a bond connecting the atoms. In addition, the sum of bonds between atoms, which linearly connect X1 and X2, is the sum of the number of bonds that connect the atoms. For example, when the number of atoms which linearly connect X1 and X2 is 17, the number of bonds is 18, and when the number of atoms is 23, the number of bonds is 24. Examples of the atom include a carbon atom, an oxygen atom and a nitrogen atom. When the sum of bonds between atoms is smaller than 18, the dispersion stability of the particles is excessively excellent based on the same mechanism as that in the case where the particles described in Japanese Patent Application Laid-Open No. 2000-351814 are used as particles for the agglutination method, and accordingly, the particles work disadvantageously for causing the agglutination reaction. On the other hand, in the case where the sum of bonds between atoms is 18 or more and 24 or less, it has been known from the studies by the present inventors that an extremely satisfactory agglutination reaction occurs when the particles of the present disclosure are used as the particles for the agglutination, though the dispersion stability of the particles is excellent. The present inventors consider that this is because of the fact that the length of a chain of the linker becomes longer than that of Japanese Patent Application Laid-Open No. 2000-351814, thereby the mobility of the reactive functional group increases in the dispersion medium, the chemical reactivity between the reactive functional group and the ligand is improved, and the reactivity between the ligand and the target substance is improved for the same reason. On the other hand, the present inventors have confirmed by an experiment that when the sum of bonds between atoms is larger than 24, an undesirable phenomenon occurs as the particles for the agglutination. The agglutination method in an immunoassay is a method of mixing an aqueous dispersion liquid of particles to which ligands are chemically bonded (hereinafter referred to as "A liquid") with a specimen that possibly contains a target substance (hereinafter referred to as "B liquid"), and optically detecting the interparticle agglutination which occurs based on a reaction between the ligand and the target substance. The inventors consider that when the sum of the interatomic bonds is larger than 24, the linker increases a tendency of embracing (solvating) a dispersion medium of the dispersion liquid thereinto, and accordingly, the nonspecific interparticle agglutination is induced which is not based on the reaction between the ligand and the target substance, due to an influence of an osmotic pressure difference which occurs when the A liquid and the B liquid have been mixed.

Specific examples of X1 or X2 of the linker A include the following formula (a1) or formula (a2).

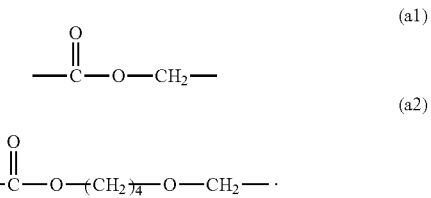

In the linker A, it is preferable that a value of a hydrogen bonding term (hereinafter δh) in a Hansen solubility parameter is 8.3 or larger and 10.5 or smaller, which is calculated when X1 and X2 are substituted with a $CH_3$ group. As the value of δh becomes smaller, the linker A shows the tendency of hydrophobicity, and as the value becomes larger, the side chain A shows the tendency of hydrophilicity. When the value of δh is smaller than 8.3, there is a possibility that the ligands are denatured with time in the particles for the agglutination method, to each of which the ligand is chemically bonded to the linker A, and the denaturation exerts an influence upon the reactivity between the ligand and the target substance. On the other hand, when the value of δh is larger than 10.5, the dispersion stability of the particles in the aqueous dispersion liquid is enhanced, and accordingly, there is the case where interparticle agglutination becomes less likely to occur in the particles for the agglutination method, to each of which a ligand is chemically bonded via the linker A. The value of δh in the present disclosure is a value that is calculated with the use of software (Soft Name: HAnsen Solubility PArAmeter in rActice; HSPiP ver.5.0.0.4) which has been developed by Hansen et al. When an estimation method using a neural network method called Y-MB is applied to the above software, and a molecular structure is input by the Smiles formula which is a molecular input line entry system, the molecule is automatically decomposed into atomic groups, and the value of δh is calculated which is a constituent component of the Hansen solubility parameter. For information, in the present disclosure, the temperature condition for calculating δh is 25° C.

It is preferable that linker A has a structure represented by the following Formula (5) or the following Formula (6). When the linker A does not have the structure represented by Formula (5) or Formula (6), in other words, when the linker A has a branched structure, an area occupied by one linker A in the surface of the particle becomes large, due to the exclusion volume effect of the linker A adjacent to each other. This fact suggests that when the linker A and the ligand are chemically bonded, there is the case where the amount of chemical bonds of the ligands per particle becomes small.

have not examined the linker A having more than 2 nitrogen atoms derived from the amine, and the contribution to the non-specific adsorption is not clarified.

It is clarified by studies of the present inventors that it is most preferable that linker A is any of the following structure A and the following structure B. The mechanism is as discussed above, and the present inventors have concluded that the above result is based on a result that the balance among various physical properties of the linker A and the particles having the linker A has been optimized.

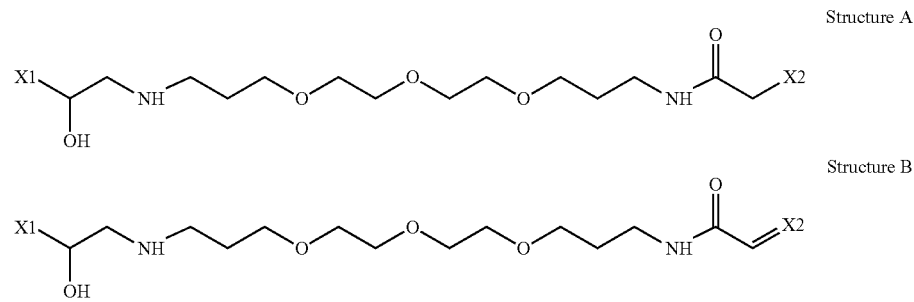

Structure A

Structure B

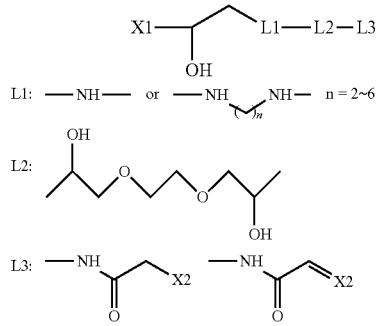

Formula (5)

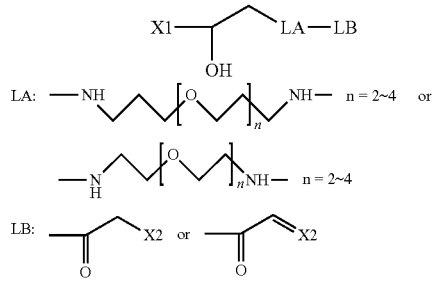

Formula (6)

When the reactive functional group is a carboxyl group or a salt of a carboxyl group, it is preferable that the linker A has a secondary or tertiary amine and the number of nitrogen atoms derived from the amine is 2 or less. It is qualitatively obvious for the purpose of suppressing the non-specific adsorption that the side chain A is more preferable as the linker A is closer to electrical neutrality. From this viewpoint, the present inventors have studied, and as a result, it has been known that when the number of nitrogen atoms at least derived from an amine is 2 or less, there is no significant concern against the non-specific adsorption. We It is preferable for the particle of the present disclosure to contain a repeating unit derived from glycidyl (meth)acrylate, and is more preferable to further contain a repeating unit of a styrene-based monomer. When the particles of the present disclosure are purified by a method such as centrifugal separation or ultrafiltration, it contributes to suppressing damage such as cracking of the particle that the particle has the repeating unit of the styrene-based monomer which has a high glass transition temperature and is excellent in a mechanical strength. Examples of the styrene-based monomers include styrene, α-methylstyrene, β-methylstyrene, o-methylstyrene, m-methylstyrene, p-methylstyrene, 2,4-dimethylstyrene, p-n-butylstyrene, p-tert-butylstyrene, p-n-hexylstyrene, p-n-octylstyrene, p-n-nonylstyrene, p-n-decylstyrene, p-n-dodecylstyrene, p-methoxystyrene and p-phenylstyrene; but are not limited to these chemical compounds in a range in which the object of the present disclosure can be achieved. In addition, two or more types of styrene-based monomers may be used in combination. It is preferable that the content of the styrene-based monomer is 10 parts by mass or more and 70 parts by mass or less when the mass of the particles is supposed to be 100 parts by mass, because a sufficient strength can be imparted to the particle while maintaining the capability of suppressing the non-specific adsorption.

The particle of the present disclosure can further contain a repeating unit derived from a radical polymerizable monomer having crosslinking properties. Examples of the radical polymerizable monomer having the crosslinking properties include diethylene glycol diacrylate, triethylene glycol diacrylate, tetraethylene glycol diacrylate, polyethylene glycol diacrylate, 1,6-hexanediol diacrylate, neopentyl glycol diacrylate, tripropylene glycol diacrylate, polypropylene glycol diacrylate, 2,2'-bis(4-(acryloxy diethoxy)phenyl) propane, trimethylolpropane triacrylate, tetramethylolmethane tetraacrylate, ethylene glycol dimethacrylate, diethylene glycol dimethacrylate, triethylene glycol dimethacrylate, tetraethylene glycol dimethacrylate, polyethylene glycol dimethacrylate, 1,3-butylene glycol dimethacrylate, 1,6-hexanediol dimethacrylate, neopentyl glycol dimethacrylate, polypropylene glycol dimethacrylate, 2,2'-bis(4-(methacryloxy diethoxy)phenyl) propane, 2,2'-bis(4-(methacryloxy polyethoxy)phenyl) propane, trimethylolpropane trimethacrylate, tetramethylolmethane tetra methacrylate, divinylbenzene, divinyl naphthalene and divinyl ether; but are not limited to these chemical compounds in a range in which the object of the present disclosure can be achieved. In addition, two or more types of radical polymerizable monomers having the crosslinking properties may be used in combination.

It is preferable for the particle sizes of the particles of the present disclosure to be 0.05 μm or larger and 1 μm or smaller, in terms of the number average particle size, is more preferable to be 0.10 μm or larger and 0.50 μm or smaller, and is further preferable to be 0.15 μm or larger and 0.30 μm or smaller. When the number average particle size is 0.15 μm or larger and 0.30 μm or smaller, the particles are excellent in workability in centrifugal separation, and are also excellent in that precipitation of particles is less likely to occur when particles are stored as a dispersion liquid for a long period of time.

The particle size of the particles of the present disclosure is a value measured under the following conditions.

Dynamic light scattering particle size measuring machine: ZETASIZER NANO ZS (manufactured by Malvern Panalytical)
Concentration of solid content: 0.01% by mass
Measurement temperature: 25° C.
Medium of dispersion liquid: Ultrapure water
Measuring cell: GlAss Cuvette
Specification of laser: He—Ne, 4 mW and 633 nm
Optical system for detection: NIBS, 173° C.
Number of measurements: 15 times
Isothermalization time period: 5 minutes
Analysis method: GenerAl Purpose Mode (cumulant method)

The method of producing the particles of the present disclosure is not limited in a range in which the object of the present disclosure can be achieved. For example, the particle can be obtained by a method of firstly producing a mother particle having a repeating unit derived from glycidyl (meth) acrylate on the surface thereof, and then chemically modifying a glycidyl group on the surface of the mother particle.

The above method of chemical modification is not particularly limited in a range in which the object of the present disclosure can be achieved, but for example, in the case of producing a particle having the linker A having the structure of Formula (5), which is one of exemplary embodiments of the present disclosure, a reaction scheme of chemical modification such as the following reaction formulae (a) to (d) can be applied.

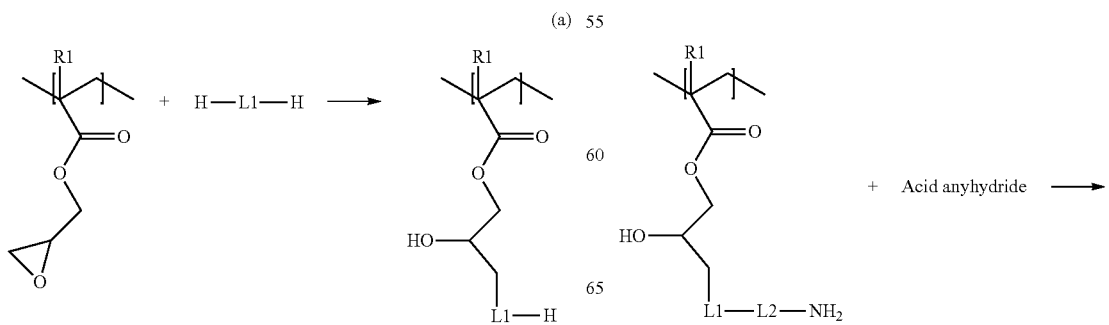

(a)

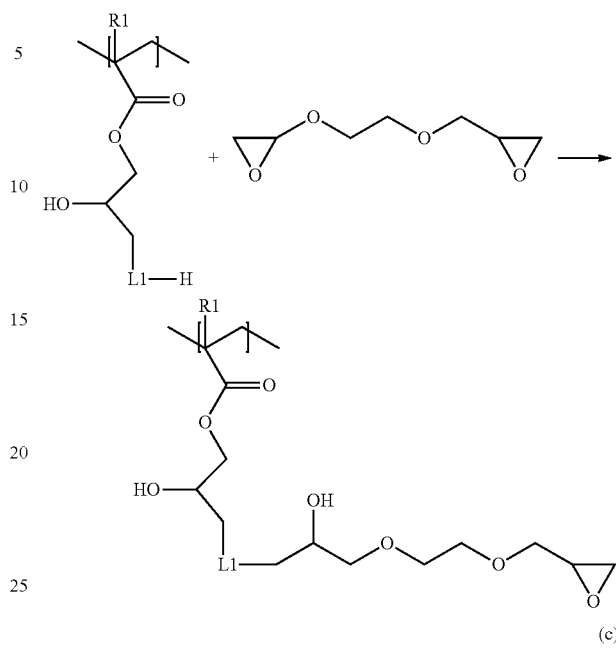

(b)

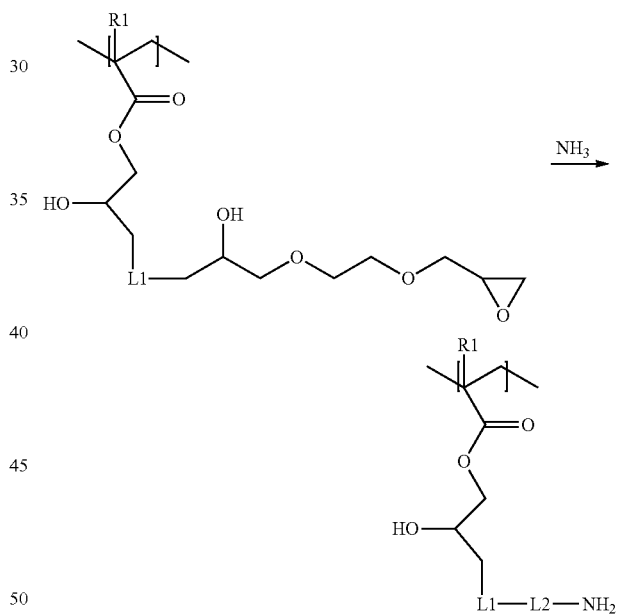

(c)

(d)

-continued

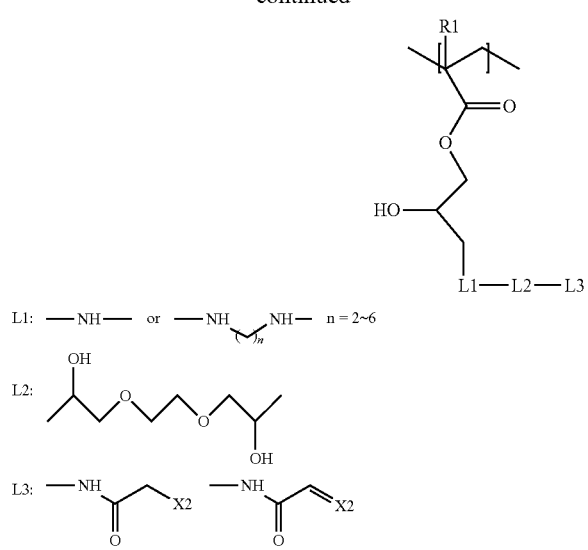

Here, R1 represents a hydrogen atom or a methyl group.

In the case of producing a particle having the linker A having the structure of Formula (6), which is one of the exemplary embodiments of the present disclosure, a reaction scheme of chemical modification such as the following reaction formulae (a') and (b') can be applied.

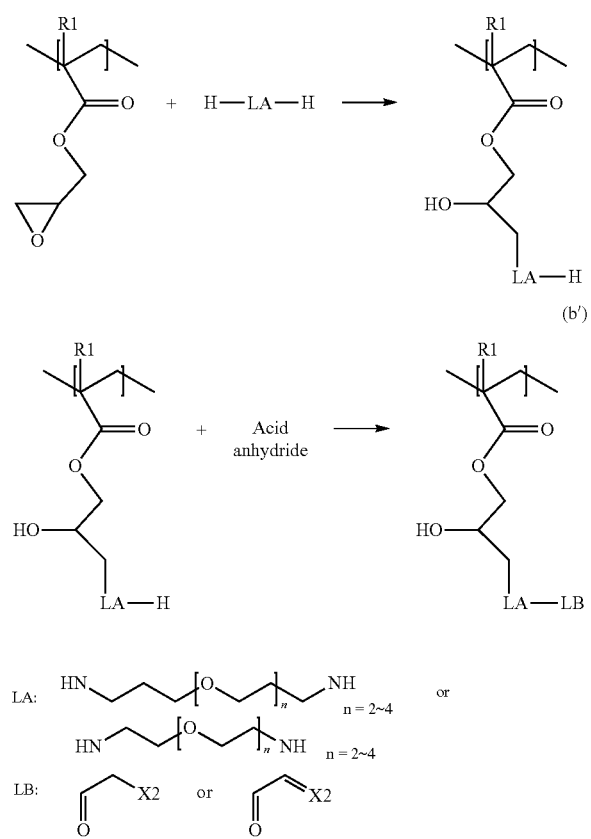

Here, R1 represents a hydrogen atom or a methyl group.

Specific examples of the structures of H-L1-H and H-LA-H are illustrated below.

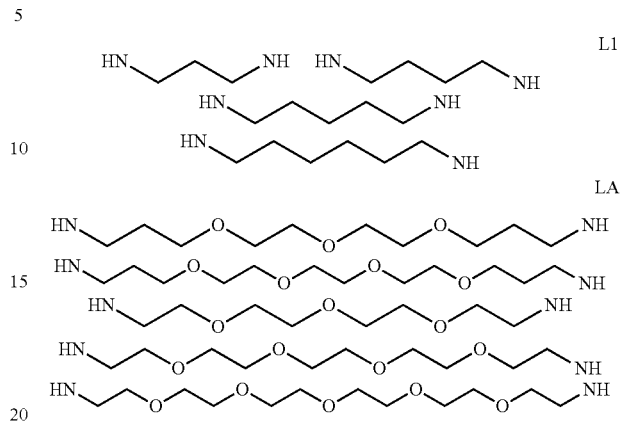

The method of producing the above mother particle is not limited in a range in which the object of the present disclosure can be achieved. It is preferable to produce the mother particles by emulsion polymerization or soap-free emulsion polymerization among radical polymerization methods, from the viewpoint of obtaining particles having a sharp particle size distribution. Hereinafter, a procedure of producing the above mother particles by the soap-free emulsion polymerization will be exemplified below, but the present disclosure is not limited to this example.

Firstly, glycidyl (meth)acrylate, a styrene-based monomer and a radical polymerizable monomer having the crosslinking properties are mixed with an aqueous medium to obtain a mixture liquid. Next, a water-soluble radical polymerization initiator is charged into the above mixture liquid, and the resultant mixture liquid is heated as necessary to proceed a radical polymerization reaction. Thereby a dispersion liquid can be formed in which the mother particles are dispersed in the aqueous medium. In the process of forming the mother particles, glycidyl (meth)acrylate may further be additionally mixed. By doing so, it becomes easy to localize more repeating units derived from polyglycidyl (meth)acrylate on the surface of the mother particle.

It is preferable that the particle of the present disclosure is a particle which contains a polymer having a unit having a side chain having a hydroxyl group at a terminal. It is preferable that the hydroxyl group exists on a surface of the particle. For example, in the case where the particle of the present disclosure is obtained by a method of firstly producing the mother particle having a repeating unit derived from glycidyl (meth)acrylate on the surface thereof and then chemically modifying a glycidyl group on the surface of the mother particle, there is the case where the glycidyl group remains on the surface of the particle, in the reaction scheme of the chemical modification of the reaction formulae (a) to (d) or the reaction formulae (a') and (b'). Because the glycidyl group has hydrophobicity, when the particle of the present disclosure is used as the particles for the agglutination method, there is a possibility that the particle results in exhibiting the non-specific adsorption properties. In addition, when particles in which the glycidyl groups remain on the surfaces of the particles are stored for a long period of time, the glycidyl groups are hydrolyzed with time, and there is a possibility that the physical properties of the particles change. For these reasons, in the present disclosure, it is preferable to chemically modify the residual glycidyl group with a chemical compound having a hydroxyl group to form a side chain having a hydroxyl group at the terminal, on the surface of the particle. Methods for forming the side chain having the hydroxyl group at the terminal are not particularly limited in a range in which the object of the present disclosure can be achieved; but include a method of chemically modifying the glycidyl group with the use of a chemical compound that has a hydroxyl group and has a functional group which chemically reacts with the glycidyl group as is shown in the following reaction formula (a″), and a method of promoting a ring-opening reaction of the glycidyl group as is shown in the following reaction formula (b″) and converting the glycidyl group to glycol.

Here, R1 represents a hydrogen atom or a methyl group, H—P represents a functional group that reacts with glycidyl, and Q represents a site having a hydroxyl group.

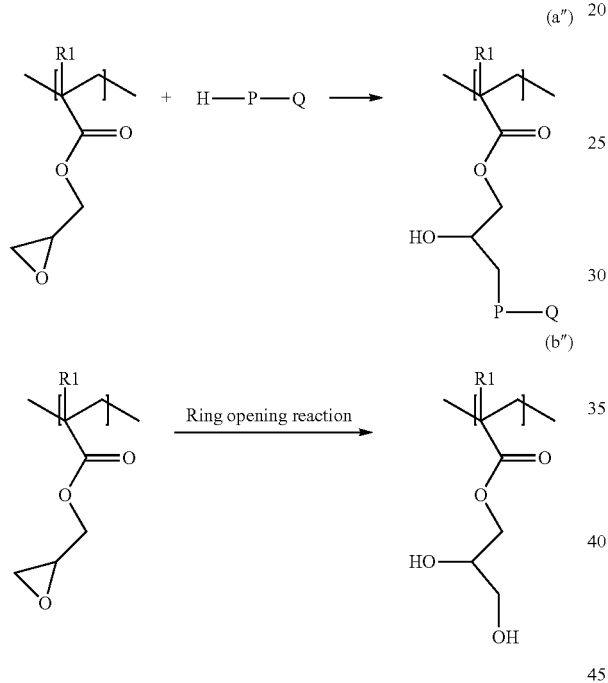

The chemical compound to be used in the reaction formula (a″) is not particularly limited in a range in which the object of the present disclosure can be achieved, but it is preferable to use a chemical compound having a thiol group having high reactivity with a glycidyl group, or a chemical compound having an amino group.

Examples of the chemical compound having the thiol group include 3-mercapto-1,2-propanediol, 2-mercaptoethanol, 3-mercaptopropanol, 1-mercapto-2-propanol, and 2-mercapto-3-butanol. In addition, examples of the chemical compound having the amino group include 2-amino-2-(hydroxymethyl)-1,3-propanediol, 2-amino-1,3-butanediol, 3-amino-1,2-propanediol, 2-amino-1,3-propanediol, 2-aminoethanol, and amino methanol.

From the viewpoint of further enhancing the performance of suppressing the non-specific adsorption properties of the particles of the present disclosure, it is more preferable to use a chemical compound having the amino group in which a chemically bonded site shows higher hydrophilicity, which will be formed by chemical modification. A plurality of the exemplified chemical compounds may be used in combination.

In the present disclosure, it is preferable that the above unit having the side chain C having a hydroxyl group at the terminal is a chemical structure of any of the following Formulae (1) to (4). In particular, Formula (2) and Formula (3) having many hydroxyl groups are extremely hydrophilic, and are very preferable as a structure for suppressing the non-specific adsorption for the particle.

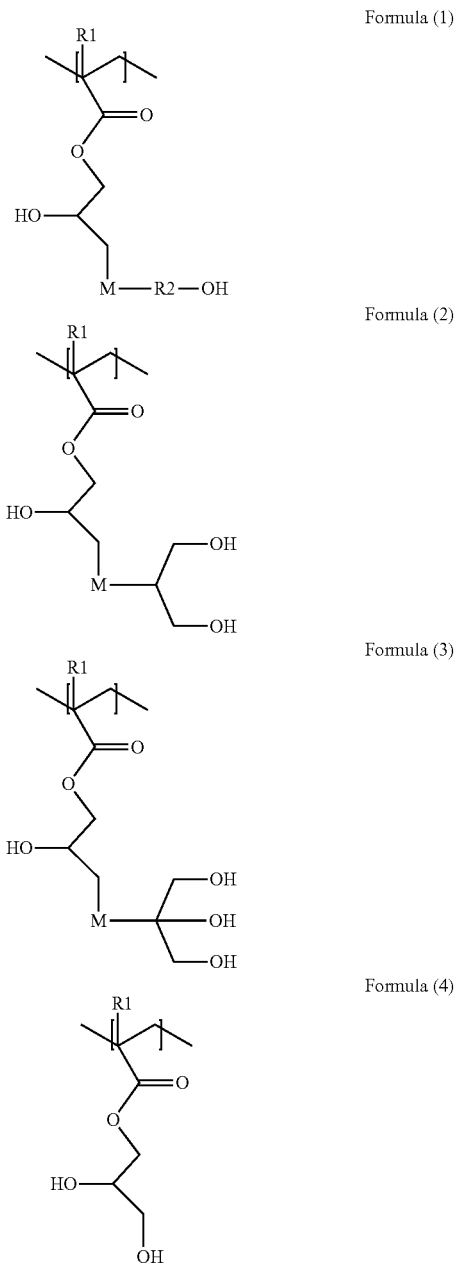

Here, M represents NH or S. In addition, R1 represents a hydrogen atom or a methyl group, and R2 represents an alkylene group.

The ligand is a chemical compound that specifically bonds to a receptor which a particular target substance has. The site at which the ligand bonds to the target substance is determined, and has a selectively or specifically high affinity. Examples of the combination of the ligand and the target substance include: an antigen and an antibody; an enzyme protein and a substrate thereof, a signal substance represented by hormones and neurotransmitters, and a receptor thereof; and a nucleic acid; but are not limited to these substances in a range in which the object of the present disclosure can be achieved. Examples of the ligands include an antigen, an antibody, an antigen bonding fragment (for example, Fab, F (ab')2, F(ab'), Fv, scFv and the like), a naturally-occurring nucleic acid, an artificial nucleic acid, an aptamer, a peptide aptamer, an oligopeptide, an enzyme and a coenzyme.

In the present disclosure, it is intended to use particles each having the above ligand chemically bonded via the linker A, as the particles for the agglutination method, which are used for the agglutination method in the immunoassay.

In the present disclosure, a conventionally known method can be applied as a method of a chemical reaction for chemically bonding a reactive functional group derived from the linker A and a ligand to each other, in a range in which the object of the present disclosure can be achieved. For example, when the reactive functional group is a carboxylic acid or a carboxylate, carbodiimide mediated reactions and NHS ester activation reactions are examples of suitable chemical reactions. However, the method of the chemical reaction for chemically bonding the reactive functional group derived from the linker A to the ligand is not limited to these chemical reactions, in a range in which the object of the present disclosure can be achieved.

In the present disclosure, when the antibody (antigen) is used as the ligand and the antigen (antibody) is used as an assessment substance, the combination can be very preferably applied to the agglutination method in the immunoassay which is widely used in the fields of clinical examinations, biochemical researches and the like, as a method of detecting the target substance in the specimen, in the in vitro diagnosis. This is because when a general particle is used as a particle for the agglutination method, an antigen (antibody) of a target substance, foreign matters in serum and the like non-specifically adsorb onto the surface of the particle, and unintended interparticle agglutination results in occurring due to this non-specific adsorption, which results in impairing the accuracy of the examination.

A reagent for use in detecting a target substance in a specimen by in vitro diagnosis of the present disclosure includes the particles for the agglutination method of the present disclosure. It is preferable for the amount of the particles for the agglutination method in the reagent of the present disclosure to be 0.001% by mass or more and 20% by mass or less, and is more preferable to be 0.01% by mass or more and 10% by mass or less. The reagent of the present disclosure may contain a third substance such as a solvent and a blocking agent, in addition to the particles for the agglutination method of the present disclosure, in a range in which the object of the present disclosure can be achieved. Examples of the solvent to be used in the present disclosure include various aqueous buffer solutions such as a phosphate buffer solution, a glycine buffer solution, Good's buffer solution, a tris buffer solution, HEPES buffer solution, a female buffer solution, and an ammonia buffer solution; but the solvent contained in the reagent of the present disclosure is not limited to these solutions.

A kit for use in detecting a target substance in a specimen by in vitro diagnosis of the present disclosure includes at least the reagent of the present disclosure. The kit of the present disclosure preferably further includes a reaction buffer solution containing albumin (hereinafter reagent 2), in addition to the reagent of the present disclosure (hereinafter reagent 1). Examples of the above albumin include serum albumin, and those which have been subjected to protease treatment may also be used. The amount of albumin contained in the reagent 2 is 0.001% by mass or more and 5% by mass or less, as a guide; but the kit of the present disclosure is not limited to this aspect. Both or either one of reagent 1 and reagent 2 may contain a sensitizer for agglutination measurement. Examples of the sensitizer for the agglutination measurement include polyvinyl alcohol, polyvinyl pyrrolidone and poly alginic acid; but the kit of the present disclosure is not limited to this aspect. In addition, the kit of the present disclosure may include a positive control, a negative control and a diluted solution of serum, in addition to the reagent 1 and the reagent 2. As a medium for the positive control and the negative control, a solvent may be used, other than serum, physiological saline and the like which do not contain a target substance that can be measured. The kit of the present disclosure can be used in the method of detecting the target substance, according to the present disclosure, similarly to the kit to be used for detecting a target substance in a specimen by ordinary in vitro diagnosis. In addition, the kit of the present disclosure can measure also a concentration of the target substance by a conventionally known method, and is suitable to be used for detecting the target substance in the specimen particularly by the agglutination method.

The method of detecting the target substance in the specimen by in vitro diagnosis, according to the present disclosure includes mixing the particles for the agglutination method of the present disclosure with the specimen that possibly contains the target substance. In addition, it is preferable to mix the particles for the agglutination method of the present disclosure with the specimen at a pH of 3.0 or higher and 11.0 or lower. In addition, the mixing temperature is 20° C. or higher and 50° C. or lower, and the mixing time period is 1 minute or longer and 20 minutes or shorter. In addition, it is preferable that a solvent is used in the present detection method. In addition, it is preferable for the concentration of the particles for the agglutination method of the present disclosure in the detection method of the present disclosure, in the reaction system, to be 0.001% by mass or higher and 5% by mass or lower, and is more preferable to be 0.01% by mass or higher and 1% by mass or lower. The detection method of the present disclosure includes optically detecting the interparticle agglutination that occurs as a result of mixing the particles for the agglutination method of the present disclosure with a specimen; and by the optical detection of the above interparticle agglutination, a target substance in the specimen is detected and the concentration of the target substance can also be measured. As for a method of optically detecting the above agglutination reaction, optical instruments may be used which can detect an intensity of scattered light, an intensity of transmitted light, an absorbance and the like, and the amounts of changes in these values may be measured.

EXAMPLES

The present disclosure will be described below in detail with reference to Examples, but the present disclosure is not limited to these Examples.

"Example 1" (Synthesis of Particle Containing Polyglycidyl (Meth)Acrylate (Particle 1))

Into a 500 ml four-necked round bottom flask, 3.60 g of styrene (St: produced by Kishida Chemical Co., Ltd.), 5.40 g of glycidyl methacrylate (GMA; Tokyo Chemical Industry Co., Ltd.), 0.12 g of divinylbenzene (Kishida Chemical Co., Ltd.) and 345 g of ion-exchanged water were weighed out to obtain a mixture liquid, and the mixture liquid was kept at 70° C. while being stirred at 200 rpm, and was subjected to nitrogen bubbling for 30 minutes. Next, the nitrogen bubbling was switched to a nitrogen flow, a solution was added to the above mixture liquid, which was separately prepared by dissolving 0.18 g of V-50 (produced by Fujifilm Wako Pure Chemical Corporation) in 15.0 g of ion-exchanged water, and thereby radical polymerization (soap-free emulsion polymerization) was started. After 2 hours from the start of the polymerization, 0.92 g of GMA was added to a reaction field of the radical polymerization, the mixture was kept at 70° C. for further 8 hours while being stirred at 200 rpm, and thereby a Dispersion liquid 1 containing the Particle 1 was obtained. The content of the 500 ml four-necked round bottom flask was slowly cooled to room temperature, then was sampled, and was subjected to the evaluation of a radical polymerization conversion rate with the use of proton NMR, gas chromatography and gel permeation chromatography. As a result, it was confirmed to be substantially 100%. The cumulant particle size of the Particle 1 was 210 nm.

"Example 2" (Synthesis of Particle 2)

Into a 200 ml four-necked round bottom flask, 20 g of the Dispersion liquid 1 was weighed out, and then was kept at 4° C. while being stirred at 100 rpm. In the state, 4.82 g in total amount of diethylene glycol bis(3-aminopropyl)ether (DEG-3APE; produced by Tokyo Chemical Industry Co., Ltd.) was mixed with the Dispersion liquid 1 at a rate of 2.0 g/min, while the mixture was irradiated with ultrasonic waves (28 kHz, 100 W) from the outside of the above 200 ml four-necked round bottom flask, and Mixture liquid 2 was prepared. After that, the Mixture liquid 2 was kept at 40° C. for 24 hours while being stirred at 100 rpm. Thereby, the glycidyl group derived from the polyglycidyl methacrylate of the Particle 1 reacted with the primary amine derived from the DEG-3APE, and Particle 2' was obtained in which the DEG-3APE was bonded to the Particle 1 at one terminal. The Particle 2' was centrifugally purified with the use of ion-exchanged water under conditions of 4° C., 27000 G, 20 minutes and 3 times. After that, the solid content was adjusted with ion-exchanged water so as to become 5 wt %, and 1.48 g of tris(hydroxymethyl)aminomethane (Tris; produced by Tokyo Chemical Industry Co., Ltd.) was further added thereto. After that, the mixture was stirred, and thereby the Tris was dissolved. Next, the pH was adjusted to 11 with triethylamine (produced by Kishida Chemical Co., Ltd.), and the mixture was stirred at 70° C. for 24 hours. After that, the resultant mixture was subjected to centrifugal separation at 4° C., at 27000 G for 20 minutes, and the supernatant was discarded. The precipitate was subjected to the purification of being redispersed by ion-exchanged water, five times in total. Next, the resultant precipitation was subjected to centrifugal purification again, was then redispersed in methanol so that the solid fraction became 1 wt %, and thereby Dispersion liquid 2" was prepared. Next, 2.77 g of succinic anhydride (produced by Tokyo Chemical Industry Co., Ltd.) was added to the Dispersion liquid 2" which was weighed out so that the Particle 2' became 0.63 g, and the mixture was shaken at 30° C. for 5 hours to thereby allow the primary amine derived from the Particle 2" to react with succinic anhydride, and the Particle 2 was obtained in which a carboxylic acid was introduced into the Particle 1 via DEG-3APE. The Particle 2 was divided into three equal parts, the parts were treated by the following three methods, and the aqueous dispersion liquids of Particle 2-1, Particle 2-2 and Particle 2-3 were obtained, which had a carboxylate of which the base is triethylamine, had a carboxylate of which the base is sodium, and did not contain a carboxylate, respectively.

(i) Method for Preparing Particle 2-1

The Particle 2 was centrifugally purified with the use of an aqueous solution of 3 wt % triethylamine under the conditions of 27000 G, 20 minutes and 3 times, and further centrifugally purified with the use of ultrapure water under the conditions of 27000 G, 20 minutes and 8 times.

(ii) Method for Preparing Particle 2-2

The Particle 2 was centrifugally purified with the use of an aqueous solution of 0.1 N NaOH under the conditions of 27000 G, 20 minutes and 3 times, and further centrifugally purified with the use of ultrapure water under the conditions of 27000 G, 20 minutes and 8 times.

(iii) Method for Preparing Particle 2-3

The Particle 2 was centrifugally purified with the use of methanol under the conditions of 27000 G, 20 minutes and 3 times, and further centrifugally purified with the use of ultrapure water under the conditions of 27000 G, 20 minutes and 8 times.

Various characteristics of the Particle 2-1 are summarized in Table 1. In addition, the dispersion stabilities of the aqueous dispersion liquids of the Particles 2-1, 2-2 and 2-3 were compared in Table 2.

"Example 3" (Synthesis of Particle 3)

An aqueous dispersion liquid of Particle 3 was obtained in the same manner as in Example 2 and Example 2(i), except that 2.68 g of maleic anhydride (produced by Tokyo Chemical Industry Co., Ltd.) was used in place of succinic anhydride. Various characteristics of the obtained Particle are summarized in Table 1.

"Example 4" (Synthesis of Particle 4)

Into a 200 ml four-necked round bottom flask, 20 g of the Dispersion liquid 1 was weighed out, and then was kept at 4° C. while being stirred at 100 rpm. In the state, 4.21 g in total amount of bis[2-(2-aminoethoxy)ethyl]ether (DEG-2AEE; produced by Tokyo Chemical Industry Co., Ltd.) was mixed with the Dispersion liquid 1 at a rate of 2.0 g/min, while the mixture was irradiated with ultrasonic waves (28 kHz, 100 W) from the outside of the above 200 ml four-necked round bottom flask, and Mixture liquid 4 was prepared. After that, the Mixture liquid 4 was kept at 40° C. for 24 hours while being stirred at 100 rpm. Thereby, the glycidyl group derived from the polyglycidyl methacrylate of the Particle 1 reacted with the primary amine derived from the DEG-2AEE, and Particle 4' was obtained in which the DEG-2AEE was bonded to the Particle 1 at one terminal. The Particle 4' was centrifugally purified with the use of ion-exchanged water under conditions of 4° C., 27000 G, 20 minutes and 3 times. After that, the solid content of the resultant particle was adjusted with ion-exchanged water so as to become 5 wt %, and 1.48 g of Tris was further added thereto. After that, the mixture was stirred, and thereby the Tris was dissolved. Next, the pH was adjusted to 11 with triethylamine, and the mixture was stirred at 70° C. for 24 hours. After that, the resultant mixture was subjected to centrifugal separation at 4° C., at 27000 G for 20 minutes, and the supernatant was discarded. The precipitate was subjected to the purification of being redispersed by ion-exchanged water, five times in total. Next, the resultant precipitation was subjected to centrifugal purification again, was then redispersed in methanol so that the solid fraction became 1 wt %, and thereby Dispersion liquid 4'' was prepared. Next, 2.77 g of succinic anhydride (produced by Tokyo Chemical Industry Co., Ltd.) was added to the Dispersion liquid 4'' which was weighed out so that the Particle 4'' became 0.63 g, and the mixture was shaken at 30° C. for 5 hours to thereby allow the primary amine derived from the Particle 4'' to react with succinic anhydride, and the Particle 4 was obtained in which a carboxylic acid was introduced into the Particle 1 via DEG-2AEE. The Particle 4 was centrifugally purified with the use of an aqueous solution of 3 wt % triethylamine under the conditions of 27000 G, 20 minutes and 3 times, and further centrifugally purified with the use of ultrapure water under the conditions of 27000 G, 20 minutes and 8 times. Thereby, an aqueous dispersion liquid of the Particle 4 was obtained. Various characteristics of the obtained Particle are summarized in Table 1.

"Example 5" (Synthesis of Particle 5)

Into a 200 ml four-necked round bottom flask, 20 g of the Dispersion liquid 1 was weighed out, and then was kept at 4° C. while being stirred at 100 rpm. In the state, 2.54 g in total amount of 1,6-hexanediamine (produced by Tokyo Chemical Industry Co., Ltd.) was mixed with the Dispersion liquid 1 at a rate of 2.0 g/min, while the mixture was irradiated with ultrasonic waves (28 kHz, 100 W) from the outside of the above 200 ml four-necked round bottom flask, and Mixture liquid 5-1 was prepared. After that, the Mixture liquid 5-1 was kept at 40° C. for 24 hours while being stirred at 100 rpm. Thereby, the glycidyl group derived from the polyglycidyl methacrylate of the Particle 1 reacted with the primary amine derived from the 1,6-hexanediamine, and Particle 5' was obtained in which the 1,6-hexanediamine was bonded to the Particle 1 at one terminal. The Particle 5' was centrifugally purified with the use of ion-exchanged water under conditions of 4° C., 27000 G, 20 minutes and 8 times. After that, the resultant precipitation was redispersed in ion-exchanged water so that the solid content became 10 wt %, and thereby Dispersion liquid 5' was prepared. Next, 3.81 g of ethylene glycol diglycidyl ether (EGDE: produced by Tokyo Chemical Industry Co., Ltd.) was added to the Dispersion liquid 5' which was weighed out so that the Particle 5' became 0.63 g, and the mixture was shaken at 30° C. for 24 hours. After that, an aqueous solution of 28% ammonia (produced by Tokyo Chemical Industry Co., Ltd.) of which the moles were 10 times those of EGDE in terms of ammonia was further added thereto, and then the mixture was shaken at 70° C. for 24 hours. Thereby, the Particle 5'' was obtained. The Particle 5'' was centrifugally purified with the use of ion-exchanged water under conditions of 4° C., 27000 G, 20 minutes and 8 times. After that, the solid content of the resultant particle was adjusted with ion-exchanged water so as to become 5 wt %, and 1.48 g of Tris was further added thereto. After that, the mixture was stirred, and thereby the Tris was dissolved. Next, the pH was adjusted to 11 with triethylamine, and the mixture was stirred at 70° C. for 24 hours. After that, the resultant mixture was subjected to centrifugal separation at 4° C., at 27000 G for 20 minutes, and the supernatant was discarded. The precipitate was subjected to the purification of being redispersed by ion-exchanged water, five times in total. Next, the resultant precipitation was subjected to centrifugal purification again, was then redispersed in methanol so that the solid fraction became 1 wt %, and thereby Dispersion liquid 5''' was prepared. Next, 2.77 g of succinic anhydride (produced by Tokyo Chemical Industry Co., Ltd.) was added to the Dispersion liquid 5''' which was weighed out so that the Particle 5''' became 0.63 g, and the mixture was shaken at 30° C. for 5 hours to thereby allow the primary amine derived from the Particle 5''' to react with succinic anhydride, and the Particle 5 was obtained in which 1,6-hexanediamine and a carboxylic acid via EGDE were introduced into the Particle 1. The Particle 5 was centrifugally purified with the use of an aqueous solution of 3 wt % triethylamine under the conditions of 27000 G, 20 minutes and 3 times, and further centrifugally purified with the use of ultrapure water under the conditions of 27000 G, 20 minutes and 8 times. Thereby, an aqueous dispersion liquid of the Particle 5 was obtained. Various characteristics of the obtained Particle are summarized in Table 1.

"Example 6" (Synthesis of Particle 6)

An aqueous dispersion liquid of Particle 6 was obtained in the same manner as in Example 5, except that 1.93 g of 1,4-butanediamine (produced by Tokyo Chemical Industry Co., Ltd.) was used in place of 1,6-hexanediamine. Various characteristics of the obtained Particle are summarized in Table 1.

"Example 7" (Synthesis of Particle 7)

An aqueous dispersion liquid of Particle 7 was obtained in the same manner as in Example 5, except that 1.32 g of ethylenediamine (produced by Tokyo Chemical Industry. Co., Ltd.) was used in place of 1,6-hexanediamine. Various characteristics of the obtained Particle are summarized in Table 1.

"Example 8" (Synthesis of Particle 8)

An aqueous dispersion liquid of Particle 8 was obtained in the same manner as in Example 5, except that 1.62 g of 1,2-propanediamine (produced by Tokyo Chemical Industry Co., Ltd.) was used in place of 1,6-hexanediamine. Various characteristics of the obtained Particle are summarized in Table 1.

"Example 9" (Synthesis of Particle 9)

An aqueous dispersion liquid of Particle 9 was obtained in the same manner as in Example 2, except that 1.11 g of 2-amino-1,3 propanediol (produced by Tokyo Chemical Industry Co., Ltd.) was used in place of Tris. Various characteristics of the obtained Particle are summarized in Table 1.

"Example 10" (Synthesis of Particle 10)

The Particle 2' obtained in Example 2 was centrifugally purified with the use of ion-exchanged water under conditions of 4° C., 27000 G, 20 minutes and 3 times. After that, the resultant precipitation was redispersed in methanol so that the solid fraction became 1 wt %, thereby a dispersion liquid was prepared, and was subjected to a reaction with succinic anhydride instead of a reaction with Tris. Other operations were performed in the same manner as in Example 2 and Example 2(i), and an aqueous dispersion liquid of Particle 10 was obtained. Various characteristics of the obtained Particle are summarized in Table 1.

"Comparative Example 1" (Synthesis of Particle 11)

An aqueous dispersion liquid of Particle 11 was obtained in the same manner as in Example 5, except that 4.82 g of DEG-3APE was used in place of 1,6-hexanediamine. Various characteristics of the obtained Particle are summarized in Table 1.

"Comparative Example 2" (Synthesis of Particle 12)

Into a 200 ml four-necked round bottom flask, 20 g of the Dispersion liquid 1 was weighed out, and then was kept at 4° C. while being stirred at 100 rpm. In the state, 28% ammonia water of which the moles are 50 times with respect to the amount of glycidyl groups contained in the Dispersion liquid 1 which was weighed out was mixed with the Dispersion liquid 1 at a rate of 2.0 g/min, while the mixture was irradiated with ultrasonic waves (28 kHz, 100 W) from the outside of the above 200 ml four-necked round bottom flask, and Mixture liquid 10-1 was prepared. After that, the Mixture liquid 10-1 was kept at 70° C. for 24 hours while being stirred at 100 rpm. Thereby, Particle 12' was obtained in which a primary amine was added to the glycidyl group derived from the polyglycidyl methacrylate of the Particle 1. The Particle 12' was centrifugally purified with the use of ion-exchanged water under conditions of 4° C., 27000 G, 20 minutes and 8 times. After that, the resultant precipitation was redispersed in ion-exchanged water so that the solid content became 10 wt %, and thereby Dispersion liquid 12' was prepared. Next, 3.81 g of EGDE was added to the Dispersion liquid 12' which was weighed out so that the Particle 12' became 0.63 g, and the mixture was shaken at 30° C. for 24 hours. After that, an aqueous solution of 28% ammonia of which the moles were 10 times those of EGDE in terms of ammonia was further added thereto, and then the mixture was shaken at 70° C. for 24 hours. Thereby, the Particle 12" was obtained. The Particle 12" was centrifugally purified with the use of ion-exchanged water under conditions of 4° C., 27000 G, 20 minutes and 8 times. After that, the solid content of the resultant particle was adjusted with ion-exchanged water so as to become 5 wt %, and 1.479 g of Tris was further added thereto. After that, the mixture was stirred, and thereby the Tris was dissolved. Next, the pH was adjusted to 11 with triethylamine, and the mixture was stirred at 70° C. for 24 hours. After that, the resultant mixture was subjected to centrifugal separation at 4° C., at 27000 G for 20 minutes, and the supernatant was discarded. The precipitate was subjected to the purification of being redispersed by ion-exchanged water, five times in total.

Next, the resultant precipitation was subjected to centrifugal purification again, was then redispersed in methanol so that the solid fraction became 1 wt %, and thereby Dispersion liquid 12''' was prepared. Next, 2.77 g of succinic anhydride (produced by Tokyo Chemical Industry Co., Ltd.) was added to the Dispersion liquid 12''' which was weighed out so that the Particle 12''' became 0.63 g, and the mixture was shaken at 30° C. for 5 hours to thereby allow the primary amine derived from the Particle 10'' to react with succinic anhydride, and the Particle 12 was obtained in which a carboxylic acid was introduced into the particle 1 via EGDE. The Particle 12 was centrifugally purified with the use of an aqueous solution of 3 wt % triethylamine under the conditions of 27000 G, 20 minutes and 3 times, and further centrifugally purified with the use of ultrapure water under the conditions of 27000 G, 20 minutes and 8 times. Thereby, an aqueous dispersion liquid of the Particle 12 was obtained. Various characteristics of the obtained Particle are summarized in Table 1.

"Comparative Example 3" (Synthesis of Particle 13)

An aqueous dispersion liquid of Particle 13 was obtained in the same manner as in Example 2 and Example 2(i), except that 3.25 g of ethylene glycol bis(2-aminoethyl) ether (produced by Tokyo Chemical Industry Co., Ltd.) was used in place of DEG-3APE. Various characteristics of the obtained Particle are summarized in Table 1.

<Evaluation of Capability of Suppressing Non-Specific Adsorption of Particle>

Dispersion liquids (A liquids) were prepared in which Particle 2-1, Particle 3, Particle 4, Particle 5, Particle 6, Particle 7, Particle 8, Particle 9, Particle 10, Particle 11, Particle 12, and Particle 13 were dispersed in phosphate buffer solutions so as to become 0.1 wt %, respectively. Next, 60 μl of a chyle solution (B solution) including triolein, lecithin, free fatty acid, bovine albumin and a Tris buffer solution was added to each of 30 μl of the Dispersion liquids, and an absorbance at a wavelength of 572 nm was measured for each of the mixture liquids immediately after stirring. The spectrophotometer GeneQuAnt1300 manufactured by Biochrom Ltd. was used for the absorbance measurement. Then, each of the mixture liquids was left at rest at 37° C. for 5 minutes, the absorbance at a wavelength of 572 nm was measured again, and the value of an amount of change in absorbance ΔABS×10000 was calculated. The results are summarized in Table 3. It is interpreted that the larger the value is, the more non-specific adsorption occurs. However, as has been described also in the embodiment, when the chain length of the linker A becomes long, the interparticle agglutination also occurs which originates from the osmotic pressure occurring when the A liquid and the B liquid have been mixed, and accordingly even if the value is large, it cannot be necessarily pronounced that the non-specific adsorption occurs. However, when the particle having the large value is chemically bonded with a ligand via a linker A and is used as a particle for the latex agglutination, the particle substantially cannot distinguish the interparticle agglutination due to the non-specific adsorption from the interparticle agglutination originating from the osmotic pressure, and it is difficult to use the particle.

<Chemical Bond Between Linker A and Ligand>

Dispersion liquids each in amount of 1 μl were prepared in which Particle 2-1, Particle 2-2, Particle 2-3, Particle 3, Particle 4, Particle 5, Particle 6, Particle 7, Particle 8, Particle 9, Particle 10, Particle 11, Particle 12, and Particle 13 were dispersed in phosphate buffer solutions so as to become 1.0 wt %, respectively. To each of these dispersion liquids, a solution was added in which 0.055 mg of 1-[3-(dimethylaminopropyl)-3-ethylcarbodiimide] (produced by Fujifilm Wako Pure Chemical Corporation) were dissolved in 10 μl of a phosphate buffer solution, then 5 μl of a dispersion liquid which contains 4.9 mg/ml of clone C5 (produced by Funakoshi Co., Ltd.) of monoclonal mouse anti-human C-reactive protein (hereinafter CRP antibody) and 5 μl of a dispersion liquid which contains 5.8 mg/ml of clone C6 (produced by Funakoshi Co., Ltd.) were added thereto, and the mixture was shaken at room temperature for 180 hours. Thereby, the reactive functional group of the linker A was chemically bonded with a ligand, and particles for the latex agglutination were obtained. Next, the particles for the latex agglutination were centrifugally purified under the conditions of 4° C., 15000 rpm, and 3 times, and finally stored as a dispersion liquid in which the resultant particles were dispersed in 1 ml of a phosphate buffer solution (hereinafter, represented by R2). Hereinafter, the names of the particles for the latex agglutination will follow the names of the particle as they are, and shall be expressed as Particles 2-1 for the latex agglutination and Particles 3 for the latex agglutination. For the purpose of comparing how different the reactivity between the reactive functional group and the ligand is, when the types of the reactive functional groups of the linker A are different, the amounts of ligands to be bonded with the Particles 2-1 for the latex agglutination, Particles 2-2 for the latex agglutination and Particles 2-3 for the latex agglutination have been summarized in Table 4.

<Evaluation of Interparticle Agglutination Properties with Respect to Human CRP Antigen>

A mixture liquid in which 1 μl of human CRP (C4063 produced by Sigma Corporation, C-reactive protein derived from human plasma, 32 mg/dl) was mixed with 50 μl of a buffer solution (buffer solution (R–1) of DENKA SEKEN, CRP-L auto "TBA") (hereinafter, represented by R1+) was prepared, and was kept warm at 37° C. In addition, a mixture liquid (hereinafter, expressed as R1−) was prepared as a control, in which 1 μl of a phosphate buffer solution was mixed with 50 μl of a buffer solution (buffer solution (R–1) of Denka Company Limited, CRP-L auto "TBA"), and was kept warm similarly at 37° C. Next, 50 μl of R2 that contained each of the particles for the latex agglutination, which were prepared in Example 10 was mixed with R1+ or R1−, and the absorbance at a wavelength of 572 nm was measured for the mixture liquid immediately after stirring. The absorbance was measured with the use of a spectrophotometer GeneQuant 1300 manufactured by Biochrom Ltd. Then, the mixture liquid was left at rest at 37° C. for 5 minutes, then the absorbance at a wavelength of 572 nm was measured again, and the value of the amount of change in the absorbance ΔABS×10000 was calculated. This series of evaluations were performed on R2 immediately after the preparation in Example 10, R2 after 24 hours after the adjustment, and R2 after 72 hours after the adjustment, respectively. The results are summarized in Table 5.

TABLE 1

| Name of particle | Example | | | | | | | | | Comparative Example | | |
| --- | --- | --- | --- | --- | --- | --- | --- | --- | --- | --- | --- | --- |
| | 2-1 | 3 | 4 | 5 | 6 | 7 | 8 | 9 | 10 | 11 | 12 | 13 |
| Sum of bonds of linker A | 20 | 20 | 18 | 24 | 22 | 20 | 20 | 20 | 20 | 31 | 17 | 15 |
| δh of linker A | 8.5 | 8.5 | 9.6 | 8.6 | 9.6 | 10.8 | 11.6 | 8.5 | 8.5 | 7.5 | 12.1 | 10.2 |
| Presence or absence of branched structure in linker A | Absent | Absent | Absent | Absent | Absent | Absent | Present | Absent | Absent | Present | Absent | Absent |
| Number of amine-derived nitrogen atoms contained in linker A | 1 | 1 | 1 | 2 | 2 | 2 | 2 | 1 | 1 | 2 | 1 | 1 |
| Particle size (nm) | 212 | 211 | 215 | 212 | 211 | 213 | 213 | 213 | 210 | 214 | 211 | 214 |

TABLE 2

| Name of particle | 2-1 | 2-2 | 2-3 |
| --- | --- | --- | --- |
| Type of reactive functional group | Triethylamine salt of carboxyl group | Sodium salt of carboxyl group | Carboxyl group |
| Dispersibility after 1 day of still standing at 4° C. | Dispersed | Dispersed | Dispersed |
| Dispersibility after 7 days of still standing at 4° C. | Dispersed | Dispersed | Settled |

TABLE 3

| Name of particle | Example | | | | | | | | |
|---|---|---|---|---|---|---|---|---|---|
| | 2-1 | 3 | 4 | 5 | 6 | 7 | 8 | 9 | 10 |
| ΔABS × 10000 | 12 | 9 | 13 | 613 | 212 | 243 | 219 | 15 | 520 |
| Assessment | excellent | excellent | excellent | fair | good | good | good | excellent | fair |

| | Comparative Example | | |
|---|---|---|---|
| Name of particle | 11 | 12 | 13 |
| ΔABS × 10000 | 1863 | 11 | 12 |
| Assessment | bad | excellent | excellent | smaller than 100: excellent
100 or larger and smaller than 500: good
500 or larger and smaller than 1000: fair
1000 or larger: bad

TABLE 4

| Name of particle | Particle 2-1 for latex agglutination | Particle 2-2 for latex agglutination | Particle 2-3 for latex agglutination |
|---|---|---|---|
| Type of reactive functional group | Triethylamine salt of carboxyl group | Sodium salt of carboxyl group | Carboxyl group |
| Amount (pieces) of ligands bonded to one particle | 1350 | 845 | 1318 |

TABLE 5

| Name of particle | | Example | | | | | | |
|---|---|---|---|---|---|---|---|---|
| | | Particle 2-1 for latex agglutination | Particle 3 for latex agglutination | Particle 4 for latex agglutination | Particle 5 for latex agglutination | Particle 6 for latex agglutination | Particle 7 for latex agglutination | Particle 8 for latex agglutination |
| ΔABS × 10000 when using R2 immediately after preparation was used | R1− | 11 | 10 | 12 | 521 | 220 | 205 | 210 |
| | R1+ | 6287 | 6378 | 4560 | 7350 | 5860 | 4840 | 3384 |
| ΔABS × 10000 when R2 after 24 hours after preparation was used | R1− | 9 | 15 | 14 | 530 | 245 | 215 | 214 |
| | R1+ | 6382 | 6257 | 4610 | 7245 | 5769 | 4956 | 3452 |
| ΔABS × 10000 when R2 after 72 hours after preparation was used | R1− | 11 | 9 | 11 | 524 | 230 | 218 | 211 |
| | R1+ | 6238 | 6302 | 4598 | 7249 | 5815 | 4980 | 3397 |

| Name of particle | | Example | | Comparative Example | | |
|---|---|---|---|---|---|---|
| | | Particle 9 for latex agglutination | Particle 10 for latex agglutination | Particle 11 for latex agglutination | Particle 12 for latex agglutination | Particle 13 for latex agglutination |
| ΔABS × 10000 when using R2 immediately after preparation was used | R1− | 13 | 515 | 1285 | 12 | 11 |
| | R1+ | 6150 | 9120 | 4650 | 2165 | 2657 |
| ΔABS × 10000 when R2 after 24 hours after preparation was used | R1− | 12 | 530 | 1455 | 14 | 17 |
| | R1+ | 6208 | 9122 | 2912 | 2120 | 2780 |

TABLE 5-continued

| ΔABS × 10000 when R2 after 72 hours after preparation was used | R1− | 14 | 545 | 1621 | 10 | 12 |
|---|---|---|---|---|---|---|
| | R1+ | 6247 | 9059 | 1895 | 2157 | 2741 |

R1−:
100 smaller than 100: excellent
100 or larger and smaller than 500: good
500 or larger and smaller than 1000: fair
1000 or larger: bad
R1+:
5000 or larger: excellent
4000 or larger and smaller than 5000: good
3000 or larger and smaller than 4000: fair
smaller than 3000: bad According to the present disclosure, there can be provided a particle of which the non-specific adsorption is small, and which has a reactive functional group for chemically bonding a ligand thereto.

Furthermore, according to the present disclosure, there can be provided a particle for the agglutination method having a ligand chemically bonded thereto; a reagent and a kit for in vitro diagnosis including the particle; and a method for detecting a target substance, with the use of the reagent and the kit.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2019-153203, filed Aug. 23, 2019 which is hereby incorporated by reference herein in its entirety.

What is claimed is:

1. A particle, comprising:
a polymer comprising a unit having a linker A in a side chain thereof,
linker A being represented by a member selected from the group consisting of formulae (5)-1, (5)-2, (6)-1, (6)-2, (6)-3 and (6)-4

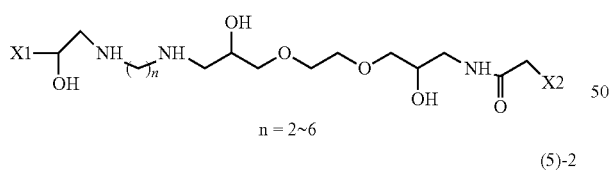

(5)-1 n = 2~6

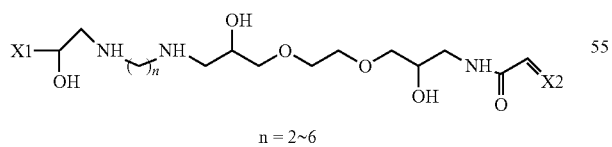

(5)-2 n = 2~6

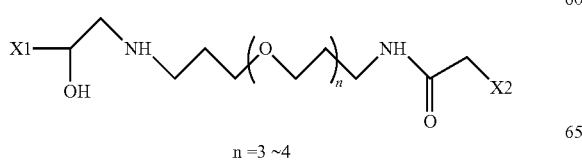

(6)-1 n = 3~4

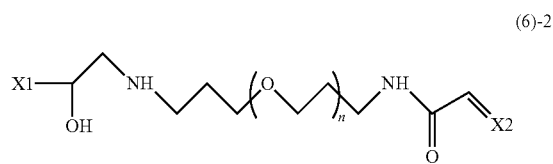

(6)-2 n = 3~4

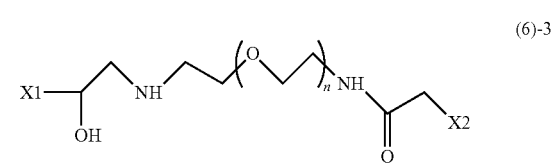

(6)-3 n = 3~4

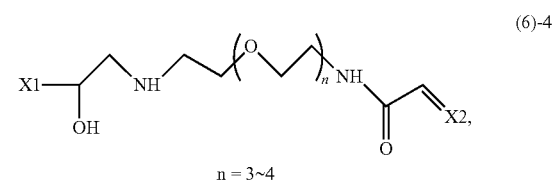

(6)-4 n = 3~4 wherein X1 comprises an ester group, X2 comprises a reactive functional group, and X1 and X2 comprise $CH_2$ or CH.

2. The particle according to claim 1, wherein the reactive functional group exists on a surface of the particle.

3. The particle according to claim 1, wherein X1 comprises a structure represented by formulae (a1) or (a2), and X2 comprises a structure represented by formulae (a1) or (a2)

(a1)

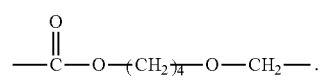

(a2)

4. The particle according to claim 1, wherein the side chain has a hydroxyl group at a terminal thereof.

5. The particle according to claim 4, wherein the hydroxyl group exists on a surface of the particle.

6. The particle according to claim 4, wherein the unit comprises a member selected from the group consisting of formulae (1) to (4)

(1) 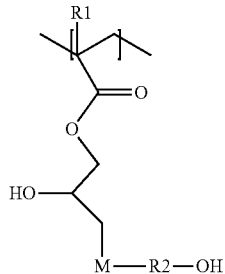

(2) 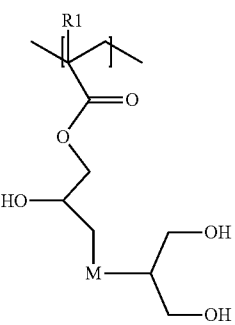

(3) 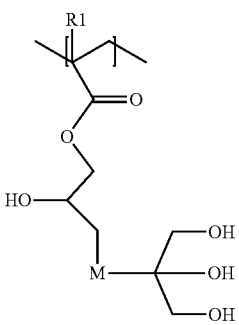

(4) 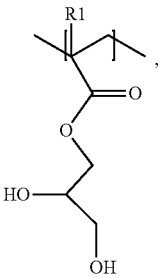

wherein M represents NH or S, R1 represents a hydrogen atom or a methyl group, and R2 represents an alkylene group.

7. The particle according to claim 1, wherein the reactive functional group is a carboxyl group or a salt of a carboxyl group.

8. The particle according to claim 7, wherein the salt of the carboxyl group is a salt that is neutralized by an organic salt.

9. The particle according to claim 1, wherein the particle comprises a repeating unit of a styrene-based monomer.

10. A particle for an agglutination method, comprising the particle according to claim 1 having a ligand bonded to the reactive functional group.

11. The particle for the agglutination method according to claim 10, wherein the ligand is an antigen or an antibody.

12. A reagent for use in detecting a target substance in a specimen by in vitro diagnosis, comprising the particle for the agglutination method according to claim 11.

13. A kit for use in detecting a target substance in a specimen by in vitro diagnosis, comprising the reagent according to claim 12.

14. An in vitro diagnostic method for detecting a target substance in a specimen, comprising the steps of:
selecting a specimen that may contain the target substance; and
mixing particles for the agglutination method according to claim 10 with the specimen that may contain the target substance.

15. A particle, comprising:
a polymer comprising a unit having a linker A in a side chain thereof,
linker A being represented by structure A or structure B Structure A

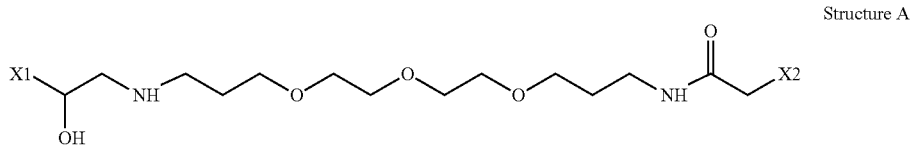

Structure B

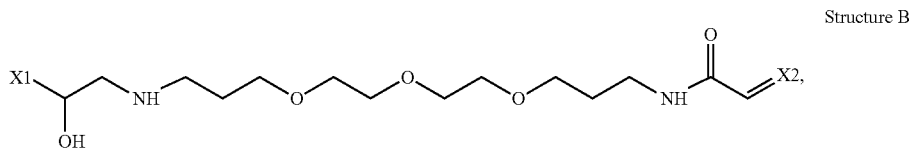

wherein one of X1 and X2 has a reactive functional group, one of X1 and X2 includes an ester group, and X1 and X2 contain CH₂ or CH.

16. A particle, comprising:
a polymer comprising a unit having a linker A in a side chain thereof,
linker A being represented by a member selected from the group consisting of formulae (5)-1, (5)-2, (6)-1, (6)-2, (6)-3 and (6)-4

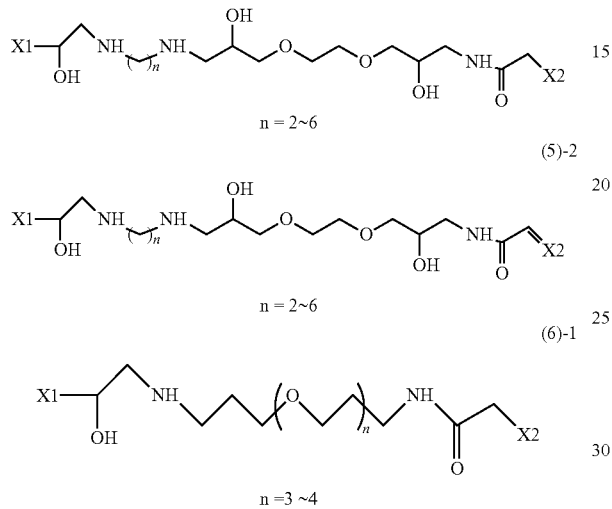

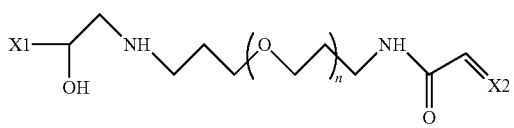

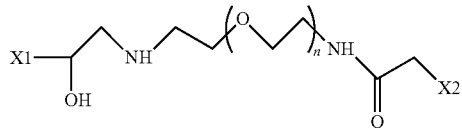

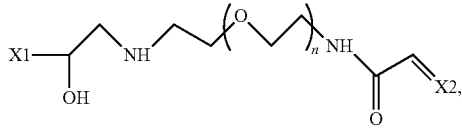

wherein
one of X1 and X2 comprises a reactive functional group,
one of X1 and X2 comprises an ester structure,
X1 and X2 comprise CH₂ or CH, and
a value of a hydrogen bonding term in a Hansen solubility parameter of CH₃-A'-CH₃ is 8.3 to 10.5, when A' indicates a structure in which X1 and X2 are removed from A.

* * * * *